(12) United States Patent
Fischer et al.

(10) Patent No.: US 10,099,980 B2
(45) Date of Patent: Oct. 16, 2018

(54) GLYCOL RECOVERY WITH SOLVENT EXTRACTION

(71) Applicant: SHELL OIL COMPANY, Houston, TX (US)

(72) Inventors: Kai Jürgen Fischer, Amsterdam (NL); Wouter Koot, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 371 days.

(21) Appl. No.: 14/893,608

(22) PCT Filed: May 28, 2014

(86) PCT No.: PCT/US2014/039667
§ 371 (c)(1),
(2) Date: Nov. 24, 2015

(87) PCT Pub. No.: WO2014/193889
PCT Pub. Date: Dec. 4, 2014

(65) Prior Publication Data
US 2016/0090342 A1    Mar. 31, 2016

Related U.S. Application Data

(60) Provisional application No. 61/829,462, filed on May 31, 2013.

(51) Int. Cl.
*C07C 29/74* (2006.01)
*C07C 29/86* (2006.01)
*B01D 11/04* (2006.01)
*C07C 29/80* (2006.01)

(52) U.S. Cl.
CPC ............. *C07C 29/86* (2013.01); *B01D 11/04* (2013.01); *B01D 11/0492* (2013.01); *C07C 29/80* (2013.01)

(58) Field of Classification Search
CPC .................................................. C07C 29/80
USPC ............................................................ 568/916
See application file for complete search history.

(56) References Cited

U.S. PATENT DOCUMENTS

| 2,831,801 A | 4/1958 | Beckham et al. |
| 4,032,583 A | 6/1977 | Arganbright et al. |
| 4,081,354 A | 3/1978 | Christman |
| 4,447,643 A | 5/1984 | Feldman |
| 4,966,658 A | 10/1990 | Berg |

(Continued)

FOREIGN PATENT DOCUMENTS

| CN | 1216973 | 5/1999 |
| CN | 101959568 | 1/2011 |

(Continued)

OTHER PUBLICATIONS

Ghanadzadeh, et al.: Experimental and Theoretical Study of the Phase Equilibria in Ternary Aqueous Mixtures of 1,4-Butanediol with Alcohols at 298.2 K j Chem Eng., 2009, 54, pp. 1009-1014.

(Continued)

*Primary Examiner* — Deborah D Carr

(57) ABSTRACT

A method of recovering an alcohol from an aqueous stream comprising: providing an aqueous stream comprising water and an alcohol; providing a solvent stream; combining the aqueous stream and the solvent stream; and recovering at least a portion of the alcohol by liquid-liquid extraction.

16 Claims, 1 Drawing Sheet

(56) References Cited

U.S. PATENT DOCUMENTS

| | | |
|---|---|---|
| 5,387,731 A | 2/1995 | Jenkins et al. |
| 5,423,955 A | 6/1995 | Berg |
| 6,023,003 A | 2/2000 | Dunning et al. |
| 8,067,214 B2 | 11/2011 | Burk et al. |
| 2005/0072663 A1 | 4/2005 | Laborie et al. |
| 2009/0171129 A1* | 7/2009 | Evanko .................. C07C 29/80 568/916 |
| 2011/0312050 A1 | 12/2011 | Zhang et al. |
| 2012/0018293 A1 | 1/2012 | Kaasa et al. |
| 2012/0184783 A1 | 7/2012 | Barnicki |
| 2013/0284584 A1 | 10/2013 | Xiao et al. |

FOREIGN PATENT DOCUMENTS

| | | |
|---|---|---|
| CN | 102295384 | 12/2011 |
| CN | 102643165 | 8/2012 |
| CN | 103396290 | 11/2013 |
| CN | 103664522 | 3/2014 |
| CN | 103772147 | 5/2014 |
| CN | 103772148 | 5/2014 |
| EP | 844228 | 5/1998 |
| JP | 2009256294 | 11/2009 |
| JP | 5640625 | 12/2014 |
| WO | 1995019946 | 7/1995 |
| WO | 2002022593 | 3/2002 |
| WO | 10080038 | 7/2010 |
| WO | 2011028131 | 3/2011 |
| WO | 2012041990 | 4/2012 |
| WO | 2012130316 | 10/2012 |
| WO | 2013011462 | 1/2013 |

OTHER PUBLICATIONS

Guan, Weihong: Heilongjiang Petrochemical Technology, vol. 11, No. 4, Dec. 31, 2000 The preparation and application of 1,4-butanediol, pp. 9-11, 1-16, 18-19.

Hoydonckx, H.E. et al.: Furfural and Derivatives, in Ulmann's Encyclopedia or Industrial Chemistry, vol. 16, pp. 285-313, 2012.

Lange, Jean-Paul, et al.; Furfural-A Promisign Platform for Lignocellulosic Biofuels, ChemSusChem 2012, pp. 150-166.

Watson J M et al.:Butane=1,4=diol from Hydrolytic Reduction of Furan.

Zeitsch, Karl. J.: The chemistry and technology of furfural and its many by-products. Elsevier, 2000.

Garcia-Chavez, et al.; "COSMO-RS assisted solvent screening for liquid-liquid extraction of mono ethylene glycol from aqueous streams", Separation and Purification Technology, vol. 97, Feb. 2012, pp. 2-10, XP002716373.

* cited by examiner

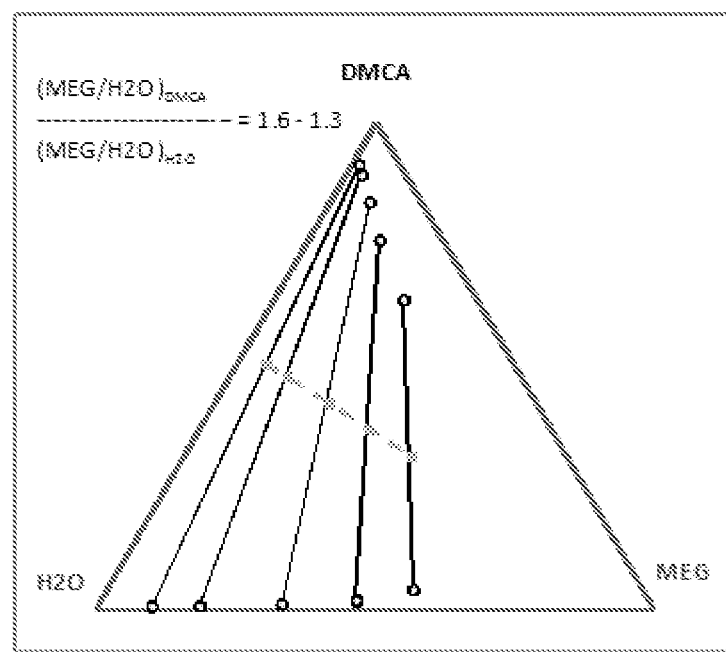

GLYCOL RECOVERY WITH SOLVENT EXTRACTION

CROSS-REFERENCE TO RELATED APPLICATIONS

The present application is a National Stage (§ 371) of International Application No. PCT/US2014/039667, filed May 28, 2014, which claims priority from U.S. Provisional Application No. 61/829,462, filed May 31, 2013, the disclosures of each of which are hereby incorporated by reference in their entirety.

BACKGROUND

The present disclosure relates generally to methods of recovering alcohols from aqueous solutions. More specifically, in certain embodiments, the present disclosure relates to solvents useful for extracting alcohols from aqueous solutions and associated methods.

The extraction of hydrocarbons from deepwater oil and gas reservoirs requires the transportation of a production stream from the reservoirs to facilities for processing. Water, along with oil and gas, may be included in these production streams. During transportation, if the temperature of the production stream is low and the pressure is high, the system can enter the hydrate region where gas hydrates form. Gas hydrates are solids and behave like ice and, if formed in large quantities, may plug the pipeline. Hydrates may also plug or cause malfunction of other units, such as valves, chokes, separators, heat exchangers, etc.

Several methods exist for limiting the formation of these hydrates in production streams. One such method is to add a hydrate inhibitor into the production stream to prevent the formation of these hydrates. An example of such a hydrate inhibitor is monoethylene glycol. Another example of such a hydrate inhibitor is methanol. The hydrate inhibitors added to the production streams may later be recovered from the product stream and recycled.

Although there are several methods for recovering the monoethylene glycol, the most commonly used in the art is boiling off the water. However, when the water is boiled off, contaminants may be left behind in the monoethylene glycol stream. These contaminants may be removed in a purification process. The most commonly used method in the art of monoethylene glycol purification is a two step process where divalent ions are knocked out of the solution with a strong alkali and a solid-liquid separation unit (e.g. a filter press) and then the solution is distilled to recover the monoethylene glycol.

These recovery and purification methods may be problematic for several reasons: (1) they require the boiling off of large quantities of water, (2) they allow for the precipitation of solids in distillation units, (3) they require a second distillation step of the monoethylene glycol before the monoethylene glycol can be recycled, and (4) they expose the monoethylene glycol to high temperatures which may cause degradation. These methods also typically have high energy requirements, costs, and footprints and typically require large chemical consumption. It is desirable to develop a method of extracting a hydrate inhibitor from an aqueous solution that does not suffer these drawbacks.

SUMMARY

The present disclosure relates generally to methods of recovering alcohols from aqueous solutions. More specifically, in certain embodiments, the present disclosure relates to solvents useful for extracting alcohols from aqueous solutions and associated methods.

In one embodiment, the present disclosure provides method of recovering an alcohol from an aqueous stream comprising: providing an aqueous stream comprising water and an alcohol; providing a solvent stream comprising an alkyl amine; combining the aqueous stream and the solvent stream; and recovering at least a portion of the alcohol by liquid-liquid extraction.

In another embodiment, the present disclosure provides a method of treating a production stream comprising: providing a production stream from a subsea oil or gas well; adding an alcohol to the production stream; adding an alkyl amine to the production stream; and recovering at least a portion of the alcohol by liquid-liquid extraction.

In another embodiment, the present disclosure provides a method of extracting an alcohol from an aqueous product stream comprising: providing an aqueous product stream comprising an alcohol; adding an alkyl amine to the aqueous product stream; and removing at least a portion of the alcohol from the aqueous product stream by liquid-liquid extraction.

BRIEF DESCRIPTION OF THE DRAWINGS

A more complete and thorough understanding of the present embodiments and advantages thereof may be acquired by referring to the following description taken in conjunction with the accompanying drawings.

FIG. 1 is a 3-component composition diagram.

The features and advantages of the present disclosure will be readily apparent to those skilled in the art. While numerous changes may be made by those skilled in the art, such changes are within the spirit of the invention.

DETAILED DESCRIPTION

The present disclosure relates generally to methods of recovering alcohols from aqueous solutions. More specifically, in certain embodiments, the present disclosure relates to solvents useful for extracting alcohols from aqueous solutions and associated methods.

The description that follows includes exemplary apparatuses, methods, techniques, and instruction sequences that embody techniques of the inventive subject matter. However, it is understood that the described embodiments may be practiced without these specific details.

There may be several potential advantages of the methods discussed herein over conventional methods. One potential advantage is that the methods discussed herein may allow for the separation and recovery of an alcohol from an aqueous stream while avoiding the large distillation duty required in a standard alcohol recovery process known in the art. Another potential advantage of the method discussed herein is that they may allow for the facile separation of alcohols either together or individually, depending on the requirements of the system.

In one embodiment, the present disclosure provides a method of recovering an alcohol from an aqueous stream comprising: providing an aqueous stream comprising water and an alcohol; combining the aqueous stream with a solvent; and recovering at least a portion of the alcohol by liquid-liquid extraction.

In certain embodiments, the aqueous stream may be any aqueous stream comprising water and an alcohol. Examples of suitable aqueous streams include production streams from subsea oil and gas wells, product streams from hydrolysis reactions of ethylene oxide, product streams from hydro liquefaction reactions of carbohydrates, and product streams from hydrolysis or esterification reactions of triglycerides.

In one embodiment, the production stream from subsea oil and gas wells may comprise a mixture of oil, gas, water, and an alcohol. Examples of alcohols included in the production stream may include monohydric alcohols and polyhydric alcohols. Examples of polyhydric alcohols include polyols such as monoethylene glycol, diethylene glycol, triethylene glycol, tetraethylene glycol, propylene glycols, butylene glycols, and glycerol. In addition, the production stream may further comprise one or more salts and one or more hydrate forming gases. Examples of salts that may be included in the production stream include sulfates, chlorides, and carbonates of potassium, sodium, magnesium, iron and calcium. In addition, salts that are formed in corrosion processes, salts used as catalysts and salts formed in acid-base neutralization reactions may be present in the production stream. Examples of hydrate forming gases that may be in the production stream include methane, ethane, propane, butane, carbon dioxide and hydrogen sulfide. Furthermore, additional additives may be included in the production stream including inhibitors and dispersants for wax, asphaltenes and scale, and corrosion inhibitors.

In certain embodiments, the water may be present in the production stream in an amount in the range of from about 0% to 100%. In other embodiments, the water may be present in the production stream in an amount in the range of from about 5% to about 50%. In other embodiments, the water may be present in the production stream in an amount in the range of from about 10% to about 25%.

In certain embodiments, the oil and gas may be present in the aqueous phase of the production stream in an amount that is between the minimum and maximum solubility of oil and gas in the aqueous phase at given conditions. In certain embodiments, the oil and gas may be present in an amount in the range of from about 0% to about 25%. In other embodiments, the oil and gas may be present in an amount in the range of from about 0.5% to about 15%. In other embodiments, the oil and gas may be present in an amount in the range of from about 1% to about 5%.

In certain embodiments, the salt may be present in the aqueous phase of the production stream in an amount that is between zero and the salt solubility limit. In certain embodiments, the salt may be present in an amount in the range of from about 0% to about 25%. In other embodiments, the salt may be present in an amount in the range of from about 0.5% to about 20%. In other embodiments, the salt may be present in an amount in the range of from about 1% to about 5%.

In certain embodiments, a portion of the oil and gas present in the production stream may be removed from the production stream before or after a glycol is added to the production stream and/or before a solvent is added to the production stream. For example, in certain embodiments, the production stream may pass through a separator to remove a portion of the oil and gas before the solvent is added to the production stream.

In certain embodiments, the alcohol may be present in, or added to, the production stream in an amount sufficient to prevent the formation of gas hydrates in the production stream as it is transported from the subsea oil and gas well to a production facility. The amount of alcohol necessary to prevent the formation of gas hydrates may depend on several factors including the pressure of the production stream, the temperature of the production stream, the water content of the production stream, the salinity of the production stream, the concentration of any additives injected in the production stream, and the concentration of hydrate forming gas in the production stream. In certain embodiments, the pressure of the production stream may be from about 0 bar to 2000 bar. In other embodiments, the pressure of the production stream may be from about 20 bar to about 500 bar. In certain embodiments, the temperature of the production stream may be from about 220 K to 500 K.

In certain embodiments, the amount of hydrate forming gas in the production stream may be from 0 mol % to 100 mol %, and typically may be from 25 mol % to 100 mol %. A person of ordinary skill in the art would be able to determine a sufficient amount of alcohol to include in the production stream to prevent the formation of gas hydrates. For example, in certain embodiments the amount of alcohol present in the production stream may be in an amount from 0% to 50%. In other embodiments, the amount of alcohol present in the production stream may be in an amount from 10% to 25%.

In certain embodiments, the product streams from hydrolysis reactions of ethylene oxide may comprise monoethylene glycol, oligomers of monoethylene glycol (for example diethylene glycol, triethylene glycol and tetraethylene glycol), ethylene oxide, water, traces of oxygenates (for example acetaldehyde, formaldehyde and methanol), carbon dioxide, catalysts (iodides, carbonates) and chlorides.

In certain embodiments, the product streams from hydro liquefaction reactions of carbohydrates may comprise water, oxygenates, hydrocarbons, catalyst, degradation products, and gases from hydrogenation reaction of carbohydrates in any composition. The variety of compounds and their concentration depend on the biomass feedstock and the various hydroliquefaction conversion options (catalysts, reaction conditions such as temperature, pressure and carbohydrate concentration. The main components may be targeted glycols such as monoethylene glycol, monopropylene glycol and 1,2-butanediol and may typically be present in an amount from 10% to 30%.

In certain embodiments, the product streams from hydrolysis or esterification reactions of triglycerides may comprise glycerol, water, methanol, fatty acids, methyl esters of fatty acids, and potassium hydroxide or sodium hydroxide from thermal or catalytic triglyceride hydrolysis or esterification. The product streams may comprise an aqueous phase with the majority of the glycerol and salt content and an organic phase with the fatty acids or fatty acid methyl esters (FAME). The aqueous phase may be from 10% to 50% of the total biphasic production stream and may have a glycerol content from 10% to 40%.

In certain embodiments, the solvent may comprise a solvent that has a higher affinity for alcohol than water. In certain embodiments, the solvent may comprise an alkyl amine. In certain embodiments, the solvent may comprise a primary, a secondary, a tertiary alkyl amine, or a combination thereof. Examples of suitable alkyl amines include paraffinic amines, naphthenic amines, aromatic amines, and mixtures thereof. Suitable alkyl amines include any amines that show a liquid-liquid phase split when mixed with water or saline water at appropriate process temperatures typically ranging from 270 K to 450 K. In certain embodiments, the solvent may comprise dimethylcyclohexyl amine, methyl cyclohexyl amine, 1-methyl piperidine, triethylamine, tripropylamine, or a combination thereof.

The solvent may be added to or combined with the aqueous stream in any amount sufficient to allow a portion of the alcohol to dissolve in the solvent. Water may also dissolve in the solvent to the extent that the alcohol to water ratio in the extract stream is larger than in the feed stream. In certain embodiments, the amount of solvent added to or combined with the aqueous stream may be from 10% to 100% of the feed amount. In certain embodiments, the ratio of solvent to alcohol may be the minimum amount for exceeding the solubility limit of the solvent in the product stream to the amount need to dissolve the entire feed stream. In certain embodiments, the amount of solvent added to or combined with the aqueous stream may be about 100% by weight of the aqueous stream.

In certain embodiments, the alcohol may be recovered from the aqueous stream by liquid-liquid extraction after the solvent has been added to or combined with the aqueous stream. In certain embodiments, the salt remains dissolved in the raffinate stream so that the separation process happens without precipitation of salts. For example, after the solvent has been added to or combined with the aqueous stream, a portion of the alcohol may be extracted into the solvent. The solvent, along with the alcohol, may then be separated from the rest of the aqueous stream forming an alcohol and solvent rich stream and a water rich stream. Typically, extraction temperatures can vary from 270 K to 450 K, where the solvent selectivity for alcohol normally increases at higher temperature. Any other components distribute between the two liquid phases. Of those components the majority of salts may stay in the aqueous phase.

In certain embodiments, the liquid-liquid extraction may be enhanced by the inclusion of a synergist. Examples of suitable synergist include demulsifiers. Typical demulsifiers can be phenol-formaldehyde resins, epoxy resins, polyamines, di-epoxides or polyols.

In certain embodiments, the method further comprises recovering alcohol and/or solvent from the alcohol rich stream. In certain embodiments, the alcohol and/or solvent may be recovered from the alcohol and solvent rich stream through a distillation process. In certain embodiments, the solvent or the alcohol may be recovered as the distillate or bottom product. In certain embodiments, the alcohol and solvent rich stream may be distilled to form an alcohol rich stream and a solvent rich stream. In certain embodiments, the alcohol and/or solvent may be recycled by recycling the alcohol rich stream and/or the solvent rich stream.

In certain embodiments the extract phase composed of N,N-dimethylcyclohexylamine, monoethylene glycol and traces of water may be distilled with pure monoethylene glycol bottom stream, pure N,N-dimethylcyclohexylamine side draw stream and the water traces separated in the distillate section.

In certain embodiments, the method may further comprise recovering a second alcohol from the aqueous stream. In such embodiments, the aqueous stream may comprise more than one type of alcohol. For example, in certain embodiments, the aqueous stream may comprise both monoethylene glycol and 1,2-butanediol. In certain embodiments, a single solvent may be selected that removes both alcohols from the aqueous product stream. The two alcohols may later be separated in a distillation process or by another liquid-liquid extraction process. In other embodiments, the aqueous stream may be treated with a first solvent to remove a portion of the first alcohol from the aqueous stream and then treated with a second solvent to remove a portion of the second alcohol from the aqueous stream. In certain embodiments, the first solvent may be more selective to the first alcohol than to the second alcohol. In certain embodiments, the second solvent may be more selective to the second alcohol than to the first alcohol. An example of a solvent that is more selective to one type of alcohol to another is dimethylcyclohexylamine, which has been shown to be more than five times more selective to 1,2-butanediol than to monoethylene glycol.

In another embodiment, the present disclosure provides a method of treating a production stream comprising: providing a production stream from a subsea oil or gas well; adding an alcohol to the production stream; adding a solvent to the production stream; and recovering at least a portion of the alcohol by liquid-liquid extraction.

In another embodiment, the present disclosure provides a method of extracting an alcohol from an aqueous product stream comprising: providing an aqueous product stream comprising an alcohol; adding a solvent to the aqueous product stream; and removing at least a portion of the alcohol from the aqueous product stream by liquid-liquid extraction.

To facilitate a better understanding of the present invention, the following examples of specific embodiments are given. In no way should the following examples be read to limit, or to define, the scope of the invention.

EXAMPLES

Example 1

To measure the partitioning of monoethylene glycol between an aqueous phase and a solvent phase, the following experiments were executed utilizing five different amines.

Brine, an amine, and monoethylene glycol were heated separately in an oven to 50° C. The brine comprised 5 wt % NaCl. The five amines tested were dimethylcyclohexyl amine, methyl cyclohexyl amine, 1-methyl piperidine, triethylamine, and tripropylamine For each amine tested, 5 bottles were filled with a mixture of brine and that amine at 1:1 ratio. Monoethyleneglycol was then added to each of the bottles in amounts varying from 5 wt % to 40 wt %.

The bottles were shaken manually and put back in an oven for overnight phase separation at 50° C. After removal from the oven, each of the bottles, with the exception of the 1-methyl piperidine with 40 wt % monoethylene glycol, had separated into two phases: a water-rich phase at the bottom and an amine-rich phase at the top.

Samples from the top and the bottom phases were taken and submitted for NMR analysis to quantify the amount of $H_2O$, monoethylene glycol, and amine in each of the phases. An indicator for the selectivity of the amine for L/L extraction of MEG was calculated by taking the $MEG/H_2O$ ratio of the top (amine) phase and dividing it by the ratio of the bottom (water) phase.

For the dimethylcyclohexyl amine bottles, the density differences between the two phases were observed to be between 0.2 and 0.15 g/mL, depending on the MEG content. The interfacial tension between DMCA and brine was observed to be between 8 and 9 mN/m. The salt content of the amine phase was observed to be between 400 and 20 times lower than the salinity of the water phase. Thus, it was determined that the presence of salt does not interfere with the extraction process and is preferentially left in the water stream.

The results of the testing of DMCA are shown in FIG. 1. Briefly, the phase compositions were plotted as a point in a ternary phase diagram (the circles in the graphs). FIG. 1 shows the analysis of the two phases in each bottle produce as two end-point compositions, connected by a tie-line that passes through the overall composition before phase separation. As can be seen in FIG. 1, the extraction of monoethylene glycol from a saline $H_2O$/MEG mixture is thermodynamically feasible.

Example 2

A solution of 10 wt % MEG in water was mixed with DMCA in a weight ratio of 1:1. This mixture was stirred at 50° C. for 30 minutes and after stopping the stirring two liquid phases quickly separated. Samples were taken from both liquid phases and analyzed by gas chromatography.

The selectivity of DMCA for MEG over water was 1.53 at 50° C.

Example 3

A solution of 10 wt % 1,2-BDO in water was mixed with DMCA in a weight ratio of 1:1. This mixture was stirred at 50° C. for 30 minutes and after stopping the stirring two liquid phases quickly separated. Samples were taken from both liquid phases and analyzed by gas chromatography.

The selectivity of DMCA for 1,2-BDO over water was 8.20 at 50° C.

Example 4

The results of Examples 2 and 3 were combined to provide a selectivity of 1,2-BDO over MEG was 5.36 at 50° C.

Example 5

A solution of 10 wt % MEG in water was mixed with DMCA in a weight ratio of 1:1. This mixture was stirred at 20° C. for 30 minutes and after stopping the stirring two liquid phases quickly separated. Samples were taken from both liquid phases and analyzed by gas chromatography.

The selectivity of DMCA for MEG over water was 1.23 at 20° C.

Example 6

A solution of 10 wt % 1,2-BDO in water was mixed with DMCA in a weight ratio of 1:1. This mixture was stirred at 20° C. for 30 minutes and after stopping the stirring two liquid phases quickly separated. Samples were taken from both liquid phases and analyzed by gas chromatography.

The selectivity of DMCA for 1,2-BDO over water was 3.93 at 20° C.

Example 7

The results of Examples 5 and 6 were combined to provide a selectivity of 1,2-BDO over MEG was 3.20 at 20° C.

Example 8

A solution of 10 wt % MEG in water was mixed with DMCA in a weight ratio of 1:1. This mixture was stirred at 90° C. for 30 minutes and after stopping the stirring two liquid phases quickly separated. Samples were taken from both liquid phases and analyzed by gas chromatography.

The selectivity of DMCA for MEG over water was 2.10 at 90° C.

Example 9

A solution of 10 wt % 1,2-BDO in water was mixed with DMCA in a weight ratio of 1:1. This mixture was stirred at 90° C. for 30 minutes and after stopping the stirring two liquid phases quickly separated. Samples were taken from both liquid phases and analyzed by gas chromatography.

The selectivity of DMCA for 1,2-BDO over water was 13.22 at 90° C.

Example 10

The results of Examples 8 and 9 were combined to provide a selectivity of 1,2-BDO over MEG was 6.30 at 90° C.

Example 11

A solution of 10 wt % MPG in water was mixed with DMCA in a weight ratio of 1:1. This mixture was stirred at 50° C. for 30 minutes and after stopping the stirring two liquid phases quickly separated. Samples were taken from both liquid phases and analyzed by gas chromatography.

The selectivity of DMCA for MPG over water was 3.10 at 50° C.

Example 12

The results of Examples 2 and 11 were combined to provide a selectivity of MPG over MEG was 2.03 at 50° C.

Example 13

The results of Examples 3 and 11 were combined to provide a selectivity of 1,2-BDO over MPG was 2.65 at 50° C.

Example 14

A solution of 10 wt % MPG in water was mixed with DMCA in a weight ratio of 1:1. This mixture was stirred at 20° C. for 30 minutes and after stopping the stirring two liquid phases quickly separated. Samples were taken from both liquid phases and analyzed by gas chromatography.

The selectivity of DMCA for MPG over water was 1.84 at 20° C.

Example 15

The results of Examples 5 and 14 were combined to provide a selectivity of MPG over MEG was 1.50 at 20° C.

Example 16

The results of Examples 6 and 14 were combined to provide a selectivity of 1,2-BDO over MPG was 2.14 at 20° C.

Example 17

A solution of 10 wt % MPG in water was mixed with DMCA in a weight ratio of 1:1. This mixture was stirred at 90° C. for 30 minutes and after stopping the stirring two liquid phases quickly separated. Samples were taken from both liquid phases and analyzed by gas chromatography.

The selectivity of DMCA for MPG over water was 5.26 at 90° C.

Example 18

The results of Examples 8 and 17 were combined to provide a selectivity of MPG over MEG was 2.50 at 90° C.

Example 19

The results of Examples 9 and 17 were combined to provide a selectivity of 1,2-BDO over MPG was 2.51 at 90° C.

Example 20

A solution of 10 wt % MEG in water was mixed with DMCA in a weight ratio of 2:1 (aqueous solution:DMCA). This mixture was stirred at 50° C. for 30 minutes and after stopping the stirring two liquid phases quickly separated. Samples were taken from both liquid phases and analyzed by gas chromatography.

The selectivity of DMCA for MEG over water was 1.03 at 50° C.

Example 21

A solution of 10 wt % 1,2-BDO in water was mixed with DMCA in a weight ratio of 2:1 (aqueous solution:DMCA). This mixture was stirred at 50° C. for 30 minutes and after stopping the stirring two liquid phases quickly separated. Samples were taken from both liquid phases and analyzed by gas chromatography.

The selectivity of DMCA for 1,4-BDO over water was 7.02 at 50° C.

Example 22

A solution of 10 wt % 1,2-BDO in water was mixed with DMCA in a weight ratio of 10:1 (aqueous solution:DMCA). This mixture was stirred at 50° C. for 30 minutes and after stopping the stirring two liquid phases quickly separated. Samples were taken from both liquid phases and analyzed by gas chromatography.

The selectivity of DMCA for 1,4-BDO over water was 6.65 at 50° C.

Example 23

The results of Examples 3, 21 and 22 were combined to show that the selectivity of 1,2-BDO over water is maintained at a high level above 6.5 even when the weight amount of solvent is only one tenth of the aqueous glycol mixture.

Example 24

A solution of 9 wt % MEG and 1 wt % 1,2-BDO in water was mixed with DMCA in a weight ratio of 10:1 (aqueous solution:DMCA). This mixture was stirred at 50° C. for 30 minutes and after stopping the stirring two liquid phases quickly separated. Samples were taken from both liquid phases and analyzed by gas chromatography.

The selectivity of DMCA for MEG over water was 1.67 at 50° C.

The selectivity of DMCA for 1,4-BDO over water was 10.595 at 50° C.

The selectivity of DMCA for 1,4-BDO over MEG was 6.36 at 50° C.

While the embodiments are described with reference to various implementations and exploitations, it will be understood that these embodiments are illustrative and that the scope of the inventive subject matter is not limited to them. Many variations, modifications, additions and improvements are possible.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

The invention claimed is:

1. A method of recovering an alcohol from an aqueous stream comprising:
    providing an aqueous stream comprising water and an alcohol, wherein the aqueous stream comprises a production stream from a subsea oil or gas well, a product stream from a hydrolysis reaction of ethylene oxide, a product stream from a hydro liquefaction reaction of a carbohydrate, or a product stream from a hydrolysis or esterification reaction of triglycerides;
    providing an alkyl amine stream;
    combining the aqueous stream and the alkyl amine stream, wherein the amount of the alkyl amine combined with the aqueous stream is an amount in a range of from 10% to 100% of the aqueous stream; and
    recovering at least a portion of the alcohol by liquid-liquid extraction comprising allowing at least a portion of the alcohol to dissolve in the alkyl amine and then separating the alkyl amine and the alcohol from the combined aqueous and alkyl amine streams to form an alcohol and alkyl amine rich stream and a water rich stream.

2. The method of claim 1, further comprising distilling the alcohol and alkyl amine rich stream to form a recovered alcohol stream and a recovered solvent stream.

3. The method of claim 2, further comprising recycling the recovered solvent stream.

4. The method of claim 1, wherein the alcohol comprises monoethylene glycol, diethylene glycol, triethylene glycol, tetraethylene glycol, propylene glycols, butylene glycols, glycerol, or a combination thereof.

5. The method of claim 1, wherein the alkyl amine comprises a primary, secondary or tertiary amine.

6. The method of claim 1, wherein the alkyl amine comprises a paraffinic amine, a naphthenic amine, an aromatic amine, or a mixture thereof.

7. The method of claim 1, wherein the alkyl amine comprises dimethyl cyclohexyl amine, methyl cyclohexyl amine, 1-methyl piperidine, triethylamine, tripropylamine, or a combination thereof.

8. The method of claim 1, wherein the aqueous stream further comprises a salt.

9. A method of treating a production stream comprising:
    providing a production stream from a subsea oil or gas well;
    adding an alcohol to the production stream;
    adding an alkyl amine to the production stream, wherein the amount of alkyl amine added to the production stream is an amount in the range of from 10% to 100% by weight of the production stream; and recovering at least a portion of the alcohol by liquid-liquid extraction comprising allowing at least a portion of the alcohol to dissolve in the alkyl amine and then separating the alkyl amine and the alcohol from the combined aqueous and alkyl amine streams to form an alcohol and alkyl amine rich stream and a water rich stream.

10. The method of claim 9, further comprising distilling the alcohol and alkyl amine rich stream to form a recovered alcohol stream and a recovered alkyl amine stream.

11. The method of claim 10, further comprising recycling the recovered alkyl amine stream and the recovered alcohol stream.

12. The method of claim 9, wherein the alcohol comprises monoethylene glycol, diethylene glycol, triethylene glycol, tetraethylene glycol, propylene glycols, butylene glycols, glycerol, or a combination thereof.

13. The method of claim 9, wherein the alkyl amine comprises a primary, secondary or tertiary amine.

14. The method of claim 9, wherein the alkyl amine comprises a paraffinic amine, a naphthenic amine, an aromatic amine, or a mixture thereof.

15. The method of claim 9, wherein the alkyl amine comprises dimethyl cyclohexyl amine, methyl cyclohexyl amine, 1-methyl piperidine, triethylamine, tripropylamine, or a combination thereof.

16. A method of extracting an alcohol from an aqueous product stream the method comprising:

providing an aqueous product stream comprising an alcohol, wherein the aqueous product stream comprises a product stream from a hydrolysis reaction of ethylene oxide, a product stream from a hydro liquefaction reaction of a carbohydrate, or a product stream from a hydrolysis or esterification reaction of triglycerides;

adding an alkyl amine to the aqueous product stream, wherein the amount of alkyl amine added to the product stream is an amount in the range of from 10% to 100% by weight of the product stream; and removing at least a portion of the alcohol from the aqueous product stream by liquid-liquid extraction comprising allowing at least a portion of the alcohol to dissolve in the alkyl amine and then separating the alkyl amine and the alcohol from the combined aqueous and alkyl amine streams to form an alcohol and alkyl amine rich stream and a water rich stream.

* * * * *